(12) United States Patent
Forsell

(10) Patent No.: US 12,290,431 B2
(45) Date of Patent: *May 6, 2025

(54) TREATMENT OF GERD

(71) Applicant: Peter Mats Forsell, Obwalden (CH)

(72) Inventor: Peter Mats Forsell, Obwalden (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/815,897

(22) Filed: Aug. 27, 2024

(65) Prior Publication Data
US 2024/0415682 A1 Dec. 19, 2024

Related U.S. Application Data

(63) Continuation of application No. 17/367,656, filed on Jul. 6, 2021, now Pat. No. 12,097,138.

(51) Int. Cl.
*A61F 2/04* (2013.01)
*A61B 17/00* (2006.01)
*A61B 17/06* (2006.01)

(52) U.S. Cl.
CPC ...... *A61F 2/04* (2013.01); *A61B 2017/00818* (2013.01); *A61B 2017/06176* (2013.01); *A61F 2002/044* (2013.01); *A61F 2002/045* (2013.01); *A61F 2230/0065* (2013.01); *A61F 2230/0071* (2013.01)

(58) Field of Classification Search
CPC .......... A61B 17/00234; A61B 17/0469; A61B 17/064; A61B 2017/00818; A61B 2017/00827; A61F 2002/044; A61F 2002/045; A61F 5/0069
See application file for complete search history.

(56) References Cited

U.S. PATENT DOCUMENTS

| | | | | | |
|---|---|---|---|---|---|
| 6,113,609 | A | * | 9/2000 | Adams | A61B 17/1114 606/139 |
| 6,463,935 | B1 | * | 10/2002 | Forsell | A61F 5/0003 128/899 |
| 7,214,233 | B2 | * | 5/2007 | Gannoe | A61F 5/0076 606/153 |
| 2005/0149072 | A1 | * | 7/2005 | DeVries | A61B 17/0469 606/153 |
| 2005/0261712 | A1 | * | 11/2005 | Balbierz | A61F 5/0036 606/153 |
| 2007/0276408 | A1 | * | 11/2007 | Filipi | A61B 17/0469 606/139 |
| 2007/0282356 | A1 | * | 12/2007 | Sonnenschein | A61B 17/068 606/153 |

(Continued)

*Primary Examiner* — Sarah W Aleman

(57) ABSTRACT

A method for affixing a fundus portion of the stomach of a human patient to the patient's esophagus is disclosed. The method comprises folding the fundus portion towards the esophagus such that the fundus portion rests against the esophagus, from the angle of His and upwards along the esophagus, and affixing the fundus portion to the esophagus by means of fasteners arranged along a first line and a second line. The first line and the second line extend along the esophagus and are arranged such that a distance between the first line and the second line increases with an increasing distance from the angle of His. The method can be used for invaginating a movement restriction device by the fundus, a position between the diaphragm and the cardiac sphincter to hinder the cardia from sliding through the diaphragm opening into the patient's thorax.

30 Claims, 8 Drawing Sheets

(56) References Cited

U.S. PATENT DOCUMENTS

| | | | |
|---|---|---|---|
| 2008/0015618 A1* | 1/2008 | Sonnenschein | A61F 5/0086 606/157 |
| 2008/0147116 A1* | 6/2008 | Smith | A61B 17/10 606/220 |
| 2012/0089157 A1* | 4/2012 | Forsell | A61F 5/0013 606/139 |

* cited by examiner

TREATMENT OF GERD

This application is a continuation of U.S. application Ser. No. 17/367,656, filed Jul. 6, 2021, the entire contents of which is hereby incorporated by reference in this application.

TECHNICAL FIELD

The present inventive concept generally relates to medical implants. More specifically the inventive concept relates to medical implants for treating gastroesophageal reflux disease (GERD).

BACKGROUND

Gastroesophageal reflux disease (GERD), or reflux disease, is a condition resulting in mucosal damage in the esophagus caused by recurring occurrence of acid reflux in the esophagus. GERD can be treated in a number of different ways, including both medical and surgical treatments. An example of a surgical treatment is Nissen fundoplication surgery, in which the upper curve of the stomach (the fundus) is wrapped around the lower esophageal sphincter (LES) to strengthen the sphincter, prevent acid reflux, and repair a hiatal hernia. This method however risks causing a constriction of the food passageway, making it more difficult for the patient to swallow.

It would therefore be advantageous to provide more efficient and/or less damaging techniques for treating GERD.

SUMMARY

It is an object of the present inventive concept to overcome, or at least alleviate, at least some of the drawbacks associated with the above-mentioned treatments of GERD. Further and/or alternative objectives may be understood from the following.

According to an aspect, a method for affixing a fundus portion of the stomach of a human patient to the patient's esophagus is provided, wherein the fundus portion extends from the angle of His and in a direction away from the esophagus. The method comprises folding the fundus portion towards the esophagus such that the fundus portion rests against the esophagus, from the angle of His and upwards along the esophagus, and affixing the fundus portion to the esophagus by means of fasteners arranged along a first line and a second line. The first line and the second line extend along the esophagus and are arranged such that a distance between the first line and the second line increases with an increasing distance from the angle of His.

According to an embodiment, the abdominal part of the esophagus and the fundus can be divided by a plane into a ventral and a dorsal side. The method may comprise providing the first line on the dorsal side of the plane and the second line on the ventral side of the plane. The first line may begin less than 1 cm above the angle of His and the second line began less than 3 cm above the angle of His. The second line may in some examples begin at a distance less than 2 cm from the first line.

According to an embodiment, a separating angle between the first line and the second line may be in the range of 90-150 degrees.

According to some embodiments, the method may comprise providing an additional fastener between the first line and the second line, at the top of the fundus portion.

In some examples, the fasteners may comprise staples. In some examples, the fasteners may comprise sutures, such as for example barbed sutures. The first line of fasteners may for example comprise a first continuous suture, and the second line of fasteners a second continuous suture.

According to some embodiments, the method may further comprises placing a movement restriction device on the fundus, forming a pouch in the fundus, arranging the movement restriction device at least partly in the pouch, and invaginating the movement restriction device by the fundus by at least partly closing the pouch by fasteners. The movement restriction device may be arranged at a position between the diaphragm and the cardiac sphincter to hinder the cardia from sliding through the diaphragm opening into the patient's thorax. The movement restriction device may be invaginated after affixing the fundus portion to the esophagus. Further, the pouch may be formed to be open in a least two positions to form a tunnel through which the movement restriction device may extend. In an example, the fundus may be affixed to the diaphragm.

Exemplary embodiments of the movement restriction device according to at least some of the above aspects will now be discussed.

According to an embodiment, a volume of the movement restriction device may be non-adjustable after implantation. According to another embodiment, the volume of the movement restriction device may be adjustable after implantation. The volume may be adjustable invasively or non-invasively. In an example, the movement restriction device comprises an injection port for allowing a fluid to be injected or extracted from the inside of the movement restriction device so as to vary the volume of the movement restriction device after implantation.

According to an embodiment, the movement restriction device may comprise a biocompatible outer surface configured to rest against the fundus wall portion. The movement restriction device may in some examples be substantially spherical or egg-shaped.

According to an embodiment, the movement restriction device may be configured to be introduced in the patient's body by means of a gastroscope or an intraluminal instrument. The movement restriction device may for example be configured to change its shape to allow it to pass through a trocar during insertion into the patient's body.

According to an embodiment, the movement restriction device may be formed of at least two distinct and separable pieces configured to be assembled into the movement restriction device after insertion in the patient's body.

According to an embodiment, a minimum width of the movement restriction device, as measured from side to side, may be 20 mm or larger, such as 30 mm or larger, such as 40 mm or larger, such as 50 mm or larger. According to an embodiment, the movement restriction device may be configured to be at least partly invaginated by the fundus at least half of the toroidal length of the movement restriction device.

According to an embodiment, the movement restriction device may be configured to be invaginated when placed on the outside of the stomach wall.

According to an embodiment, the movement restriction device may comprise two end portions configured to be coupled to each other to form a closed ring. The end portions may be configured to be releasably attached to each other.

According to an embodiment, the movement restriction device may have a shape conforming to a torus.

According to an embodiment, the movement restriction device may have C-shaped cross section.

According to an embodiment, a poloidal circumference of the movement restriction device may be larger for the first portion and for the second portion. In an example, a minimum width of the first portion of the movement restriction device, as measured from side to side, is 20 mm or larger, such as 30 mm or larger, such as 40 mm or larger, such as 50 mm or larger. Alternatively, the width may be defined as a height measured along a normal to the plane in which the circumference extends.

According to an embodiment, an upper portion of the movement restriction device may comprise a recess defined in the outer surface of the movement restriction device.

According to an embodiment, a lower portion of the movement restriction device may comprise a curved outer surface, which may be arranged to face the esophagus. The curved outer surface may comprise a radius of curvature corresponding to or exceeding the radius of curvature of the esophagus.

According to an embodiment, an outer surface of the movement restriction device may comprise a material for hindering growth of fibrotic tissue.

The various apparatuses and methods according to the above aspects can be combined with any of the features, examples and effects described in the present application.

BRIEF DESCRIPTION OF THE DRAWINGS

The above, as well as additional object, features and advantages of the present inventive concept will be better understood through the following illustrative and non-limiting detailed description, with reference to the appended drawings.

DETAILED DESCRIPTION

Figure 1:
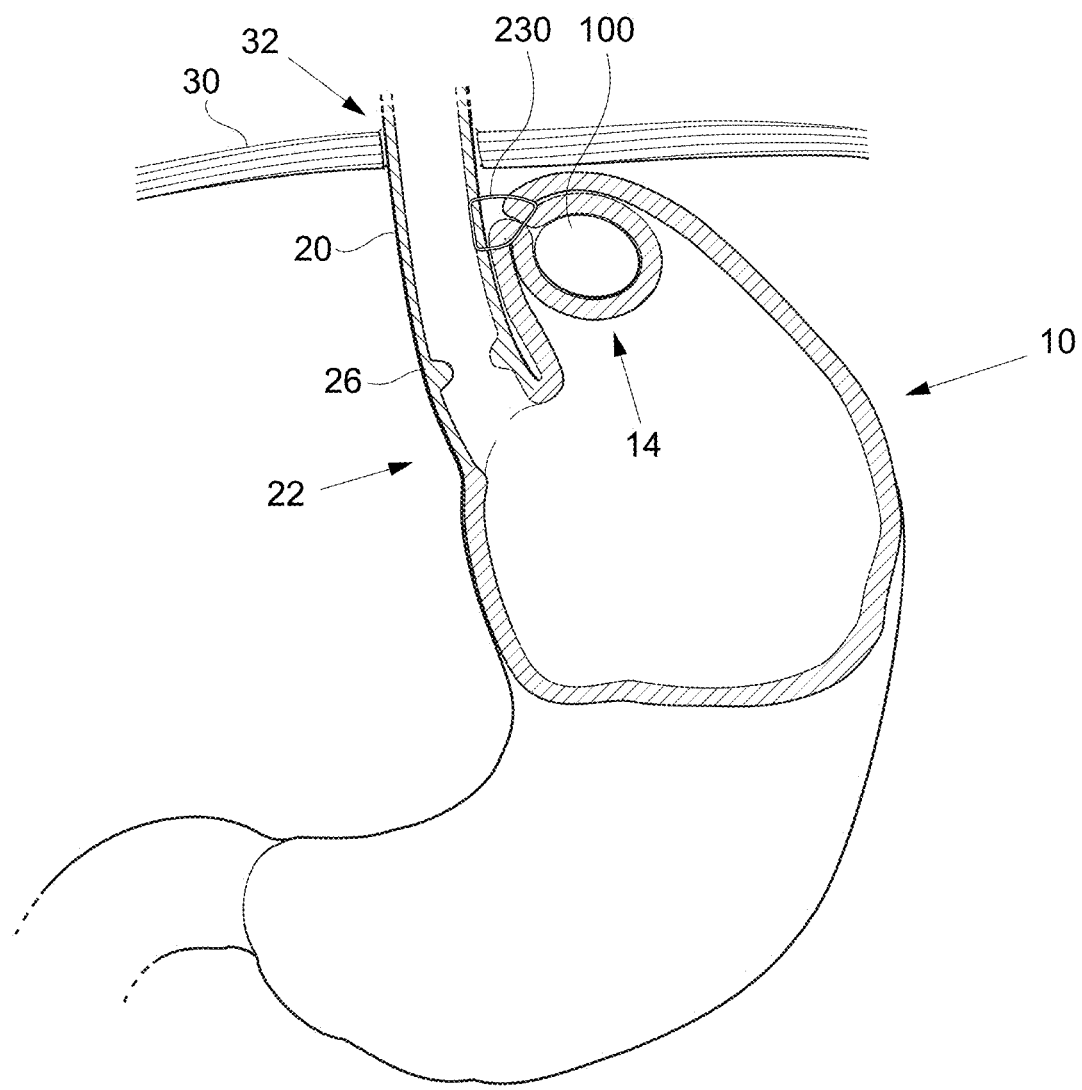
FIGS. 1-6 are schematic views of various examples of apparatuses for treating reflux disease, wherein the apparatuses are implanted in the body of the patient.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, a feature in one embodiment could thus be exchanged for a feature from another embodiment having the same reference numeral unless clearly contradictory. The descriptions of the features having the same reference numerals should thus be seen as complementing each other in describing the fundamental idea of the feature and thereby showing the features versatility.

FIG. 1 is a schematic illustration of an apparatus 100 according to some embodiments of the present disclosure. The apparatus 100 may be used for treatment of a human patient suffering from gastroesophageal reflux 30 disease (GERD), also referred to as reflux disease. As illustrated in the present figure, the apparatus 100 may comprise a movement restriction device 110 configured to be implanted in the stomach 10 for hindering the cardia 22 from sliding through the diaphragm opening 32. The apparatus 100 may be invaginated in the fundus 12 using a similar method as the one described with reference to FIGS. 7a-c and 8a-b. It will however be appreciated that the apparatus can be implanted using other methods as well, and that the following figures therefore merely should be considered to represent illustrating and non-limiting examples.

The movement restriction device 110 may be arranged to rest against a fundus wall portion 14 of the stomach 10. In the present example, the movement restriction device 110 is arranged to rest against the outside of the stomach wall. The movement restriction device 110 may have a shape and size that allows it to be fully or at least partly invaginated by the fundus wall portion 14. This may be achieved by forming a pouch or recess in the fundus wall portion 14 and at least partly closing the opening of the pouch or recess so as to hinder the movement restriction device 110 to be removed from the fundus wall portion 14. The invagination by the fundus wall portion 14 allows for the movement restriction device 110 to be implanted at a position between the patient's diaphragm 30 and a lower portion of the fundus wall 12, such that movement of the cardia 22 towards the diaphragm 30 is restricted. By restricting this movement, the cardia 22 may be hindered from sliding up towards, and possibly through, the diaphragm opening 32 into the patient's thorax, and the supporting pressure against the cardiac sphincter 26 exerted from the abdomen can therefore be maintained. Advantageously, the method outlined in connection with FIGS. 7a-c may be used so as to attach a part of the stomach wall to the esophagus, prior to invaginating the device, so as to provide a "platform" positioning the movement restriction device at the desired height.

As illustrated in the example in FIG. 1, the movement restriction device 110 may hence be coupled, of affixed to the esophagus 20 at a position above the cardiac sphincter 26. The affixation of the movement restriction device 110 may preferably be of an indirect nature, achieved by affixing a part of the fundus 14 to the esophagus 20 such that the invagination can act as a mechanical stop against the diaphragm 30 when the esophagus is moving upwards through the diaphragm opening 32. Further, in order to protect the tissue of the esophagus 20 from being damaged by the movement restriction device 110, the movement restriction device 110 may be implanted such that a part of the fundus is arranged between the movement restriction device 110 and the outside of the esophagus 20.

The shape and size of the movement restriction device 110 is an important factor for allowing the invagination to act as a mechanical stop against the diaphragm 30. Preferably, the movement restriction device 110 may have a size and shape that allows for the invagination to be sufficiently large to hinder the fundus wall portion 14 to slide through the diaphragm opening 32 together with the cardia. Further, the movement restriction device 100 may have a size and shape that allows it to be invaginated by the fundus 12 of the stomach without causing an unjustified reduction of the total volume of the stomach cavity. In addition to this, the movement restriction device 100 may at the same time be sufficiently small to allow it to generate a mechanical stop against the diaphragm muscle while leaving the food passageway substantially intact and unaffected. Thus, the movement restriction device 100 disclosed herein advantageously allows for the symptoms of reflux disease to be addressed while reducing the risk for compressing the food passageway.

To facilitate invagination and reduce the risk for damaging the tissue of the fundus wall portion 14 the movement restriction device 110 may have a substantially smooth outer surface. Any corners, edges, joints, or seams may be rounded so as not to damage or irritate the tissue against which the movement restriction device 110 may rest when implanted. In some examples the movement restriction device 110 may have a rounded shape, for example conforming to a sphere, a spheroid, or an egg.

The minimum width of the movement restriction device 110, as measured from side to side, may in some examples be 30 mm or larger, such as 40 mm or larger. Additionally, or alternatively a minimum outer circumference of the movement restriction device 110 may be 150 mm or less, such as 130 mm or less, such as 110 mm or less. In further examples, the minimum outer circumference may be 90 mm or less, such as 70 mm or less, such as 50 mm or less, and such that 30 mm or less. It will however be appreciated that the dimensions of the movement restriction device may vary according to the anatomy of the actual individual into which the movement restriction device 110 is to be implanted. The size and shape of the movement restriction device 110 may be adapted to the individual patient to allow for the invagination to act as a mechanical stop as outlined above and thereby have an effect on reflux disease.

The movement restriction device 110 may be formed of a biocompatible material that is suitable for long-term implantation in the human body. Alternatively, or additionally, the outer surface of the movement restriction device 110 may be provided with a layer or coating of such a material. Examples of biocompatible materials include titanium or a medical grade metal alloy, such as medical grade stainless steel. In an alternative, movement restriction device 110 may be made from of comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). Movement restriction device 110 could also comprise at least one composite material, such as any combination of metallic/ceramic and polymer materials or a polymer material reinforced with organic or inorganic fibers, such as carbon or mineral fibers. Further, the movement restriction device may comprise an enclosure made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass.

Further, the movement restriction device 110 may according to some examples be configured to be introduced into the patient's body by means of a gastroscope or an intraluminal instrument, thereby allowing the apparatus 100 to be implanted by means of natural orifice transluminal endoscopic surgery (NOTES). Hence, the movement restriction device 110 may have a shape and size allowing it to be introduced and pass through a tubular instrument. In some examples, the movement restriction device 110 may be configured to change its shape, preferably resiliently, to temporarily assume a smallest width that allows for the movement restriction device 110 to pass through such an instrument.

In FIG. 1 the movement restriction device 110 is invaginated in the fundus wall portion 14 from outside the stomach. A plurality of stomach-to-stomach sutures or staples may be applied to maintain the invagination intact and the movement restriction device 110 in the desired position relative to the cardia 22 and the diaphragm 30 of a standing patient. This allows for a growth of fibrotic tissue for keeping the invagination intact over time.

Figure 2:
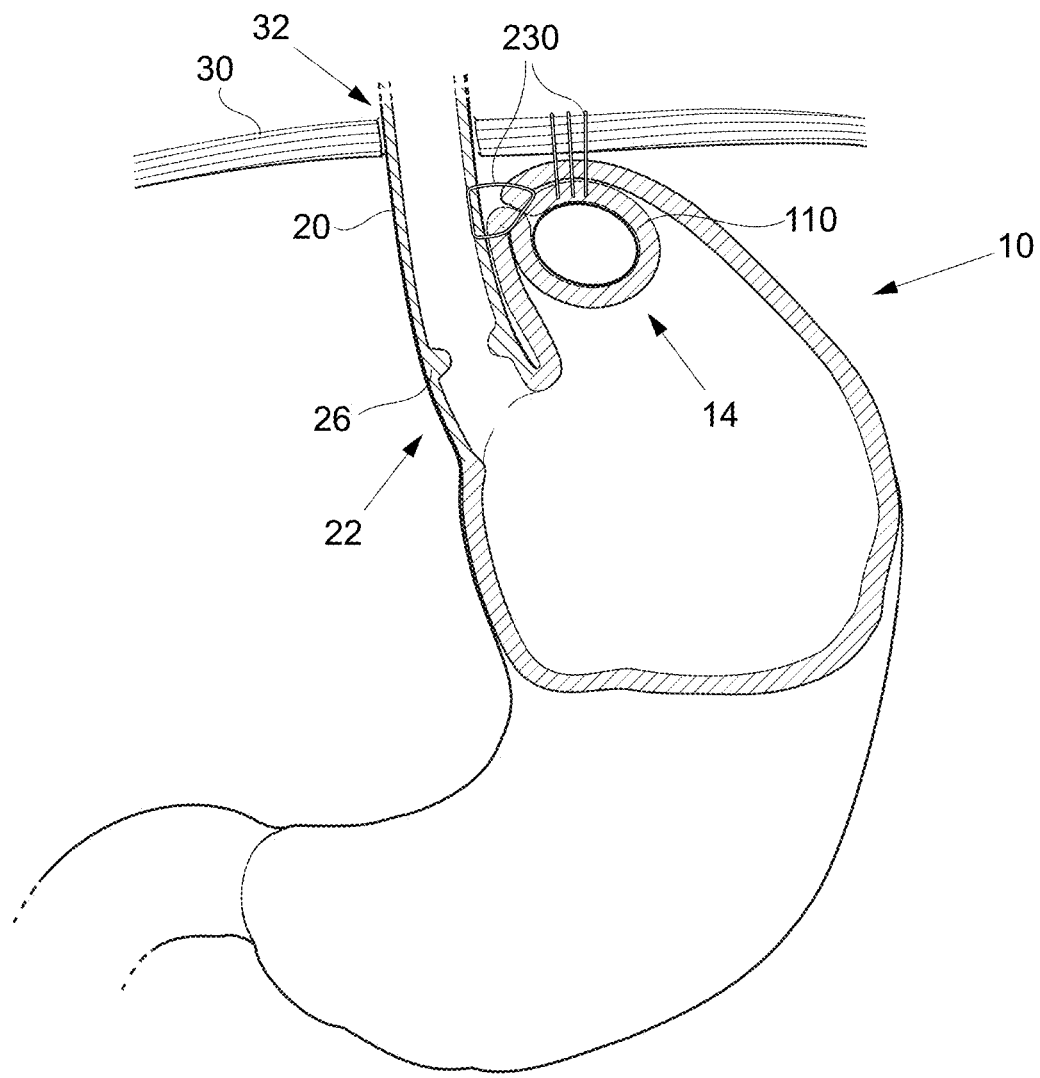

Additionally, or alternatively, an affixation may be provided between the fundus wall portion 14 and the diaphragm 30, and/or the fundus wall portion 14 and the esophagus 20 as illustrated in FIG. 2. The movement restriction device 110 depicted in FIG. 2 may be similarly configured as the embodiments discussed in connection with FIG. 1, and FIG. 2 hence discloses a movement restriction device 110 implanted in in the fundus 12 and arranged at a position above the cardia 22 so as to provide a mechanical stop reducing the symptoms of reflux disease.

Figure 3:
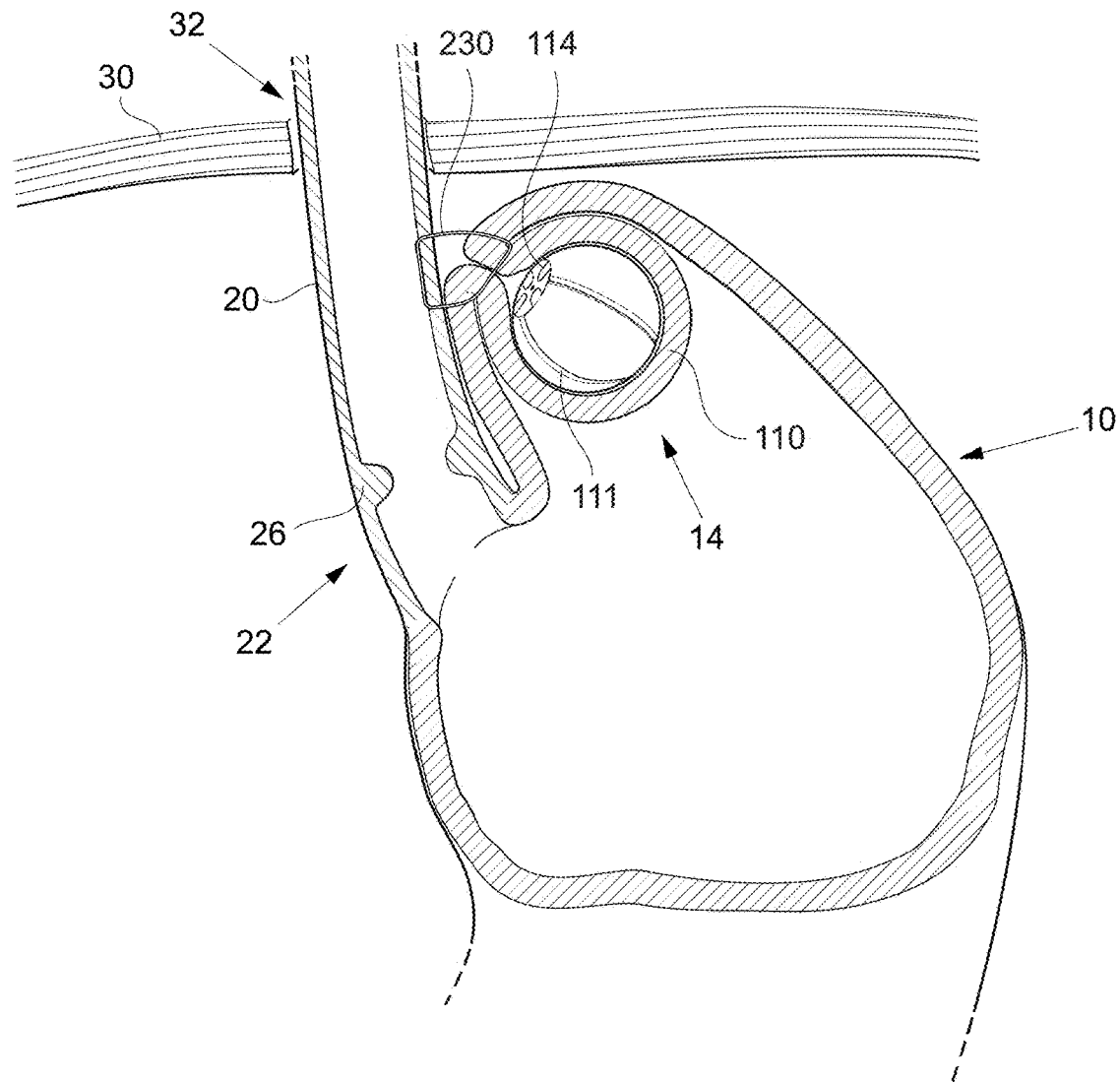

The movement restriction device 110 disclosed in FIGS. 1 and 2 may have several different configurations and may not necessarily be limited to the schematic versions outlined therein. Other configurations and designs are conceivable within the inventive concept, as defined by the appended claims. An example of such a variant is illustrated in FIG. 3, showing a movement restriction device 110 similar to the ones in FIGS. 1 and 2 but formed of a plurality of segments 111 that are configured to be attached to be assembled into a complete movement restriction device 110. The segments 111 may for example be secured to each other by means of mutually engaging structures 114 such as protruding slits and receiving grooves, snap-fit connectors, or the like. In the present example, the movement restriction device 110 may be formed of five segments 111: four outer parts 112 and an inner, core part 113 around which the outer parts 112 may be arranged to form a rounded and substantially smooth body suitable for invagination. The segments 111 may be configured to be securely attached to each other, or to be loosely fitted and kept in their right position when invaginated by the surrounding fundus wall 12. In some examples, the segments 111 may be secured to each other by means of a wire. The wire may be biodegradable and eventually dissolved. The segments 111 may be configured to be introduced in the body of the patient separately, one by one, and assembled into the movement restriction device 110 in connection with being implanted.

The movement restriction device 110 according to any of the above-mentioned examples may have a volume that is adjustable or non-adjustable after implantation. In case of a non-adjustable volume, the movement restriction device 110 may be formed of a body (or several segments) being solid, i.e., which is not hollow and/or comprises substantially the same material throughout. This may allow for the shape to be varied, for example during insertion into the body, such as through a tubular instrument, while the volume may be substantially the same. In case the movement restriction device 110 is adjustable in terms of volume, the device may be formed of a body (or several segments) comprising one or several cavities or voids capable of accumulating an releasing a fluid for causing a corresponding expansion and reduction of the movement restriction device 110. The fluid may for example be a gas or a liquid, such as a gel, which may be introduced and extracted from the movement restriction device 110 prior to implantation, during the implantation procedure, or after it has been implanted.

Figure 4A:
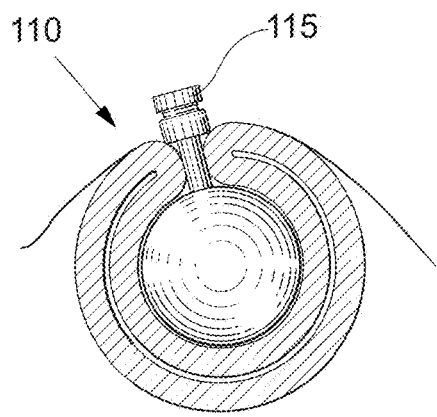
Figure 4B:
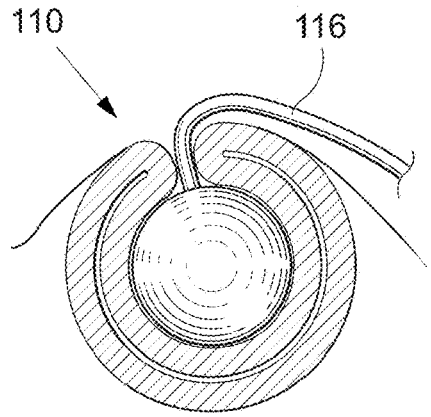

FIGS. 4a and 4b illustrate an example of a movement restriction device 110, similar to the ones discussed with reference to FIGS. 1-3, comprising a fluid communication port 115, or injection port, that can be used to add or remove a fluid to/from the inside of the movement restriction device 110 to thereby vary its volume. It may be desired to adjust the volume of the movement restriction device 110 postoperatively in order to fine tune or adjust the movement restriction device's 110 capability of acting as a mechanical stop against the diaphragm. It may for example be determined after the implantation, in a subsequent evaluation of the results of the operation, that an implant of another size would have been more optimal for the specific patient. This may be solved by adjusting the volume of the implant posit-operatively.

As shown in the present figures, the port 115 may be positioned such that it is accessible from outside the invagination, i.e., such that the port 115 can be accessed by an instrument or connection without having to penetrate the fundus wall portion 14. In FIG. 4a the port protrudes to the outside of the invagination, passing between sutures or staples used for at least partly closing the pouch in which the movement restriction device 110 is arranged. The port 115 may thus be available for connection to a tube or a syringe from the abdominal region of the patient. In FIG. 4b the port 115 is positioned inside the invagination and accessed by a tube 116 that is connected to the port 115 and extends into the abdominal region of the patient.

The volume of the movement restriction device 110 may according to some examples be adjustable non-invasively after implantation. A non-invasive adjustment may be allowed by means of the tube 116, that may be connected to the port 115 and led to the outside of the patient's body or to an implanted volume regulator, such as a pump or a reservoir, for non-invasive regulation of the volume of the movement restriction device 110. According to other examples, the volume of the movement restriction device 110 may be adjustable invasively, e.g. by means of an instrument that is inserted into the patient's body and connected directly to the port 115 or the tube 116 for adding or removing fluid from the movement restriction device 110. Alternatively, or additionally, an instrument such as a syringe may be inserted directly into the inside of the movement restriction device 110, penetrating and passing through the surrounding fundus wall portion 14 on the way to the movement restriction device 110.

It will be appreciated that the adjustable and non-adjustable characteristics of the volume of the movement restriction device 110 generally refer to a permanent state of the movement restriction device 110. In other words, an adjustment of the volume may, in the above context, result in a new volume that is substantially constant over time until the amount of fluid in the movement restriction device 110 is varied again. This may be contrasted with temporary changes of the volume, which for example may be caused by a temporary or resilient compression of the material forming the movement restriction device 110. Such a temporary change in volume may for example occur during introduction of the movement restriction device 110 into the body, e.g. via a tubular instrument. In other words, the movement restriction device 110 according to the examples outlined above with reference FIGS. 1-4 may be flexible or elastic, allowing the device 110 to at least temporarily assume different shapes and, in some examples, volumes, in response to being exposed to external mechanical forces.

Figure 5:
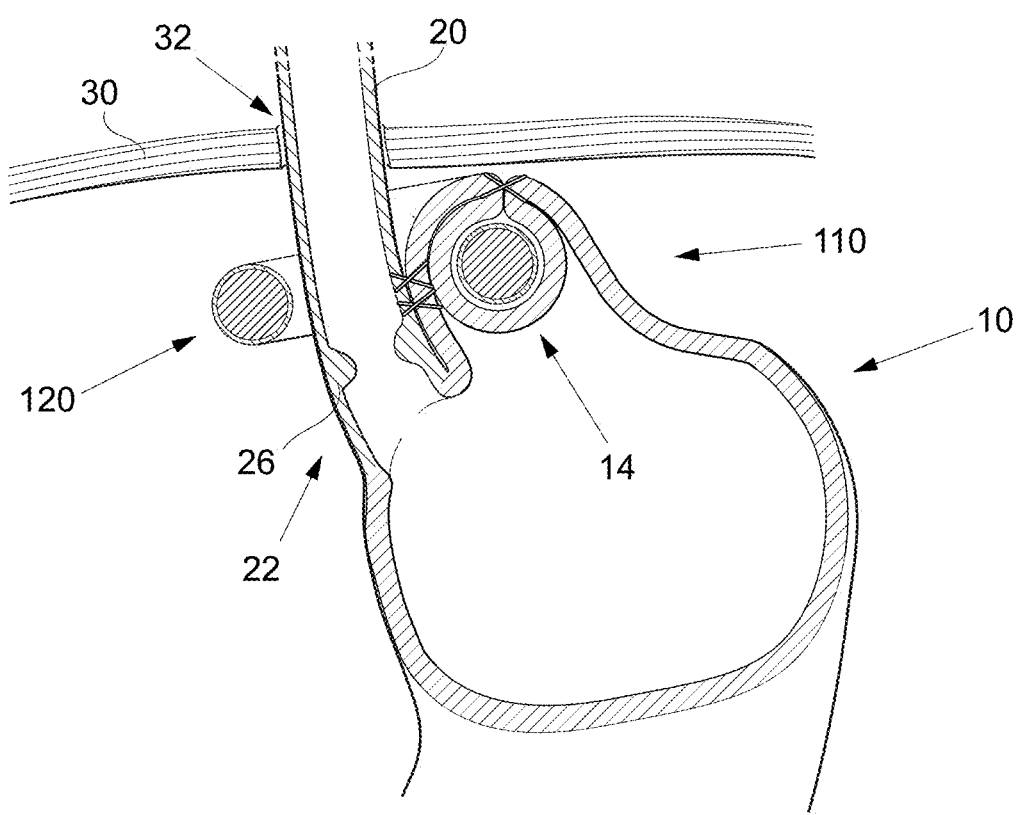

A further example of an apparatus for treating reflux disease, as outlined above, will now be described with reference to FIGS. 5 and 6. The figures schematically illustrate an apparatus 100 comprising an at least partly ring-shaped implantable movement restriction device comprising a first portion 110 configured to be at least partly invaginated by a first wall portion of the patient's stomach 10 and arranged such that at least a part of the first portion of the apparatus 100 is arranged above the cardia 22 of the patient's stomach 10, and such that movement of the cardia towards the diaphragm is restricted to prevent the cardia 22 from sliding through the diaphragm opening 32 into the patient's thorax. The configuration and function of the first portion 110 of the apparatus 100 may hence be similar to the movement restriction devices 110 previously described with reference to FIGS. 1-4, and may advantageously be implanted using the method outlined in connection with FIGS. 7a-c and 8a-b.

The apparatus 100 may further comprise a second portion 120, which may be configured to be arranged on an opposite side of the cardia 22, as seen from the first portion 110. The first portion 110 and the second portion 120 may together form the at least partly ring-shaped movement restriction device 110, 120, which as indicated in FIG. 5 may be configured to be arranged to at least partly encircle the esophagus 20 of the patient. The first portion 110 may for example be configured to be arranged on the fundus side of the esophagus 20, whereas the second portion 120 may be configured to be arranged on the side of the esophagus 20, i.e., the side opposing the fundus 12. The movement restriction device 110 may in some examples be formed of a substantially smooth, ring-shaped body configured to encircle the esophagus 20. The movement restriction device 110 may for example have a shape conforming to a torus, with the first portion 110 forming the part arranged at the fundus side of the esophagus and the second portion 120 forming the part arranged at the opposite side of the esophagus 20.

Figure 6:
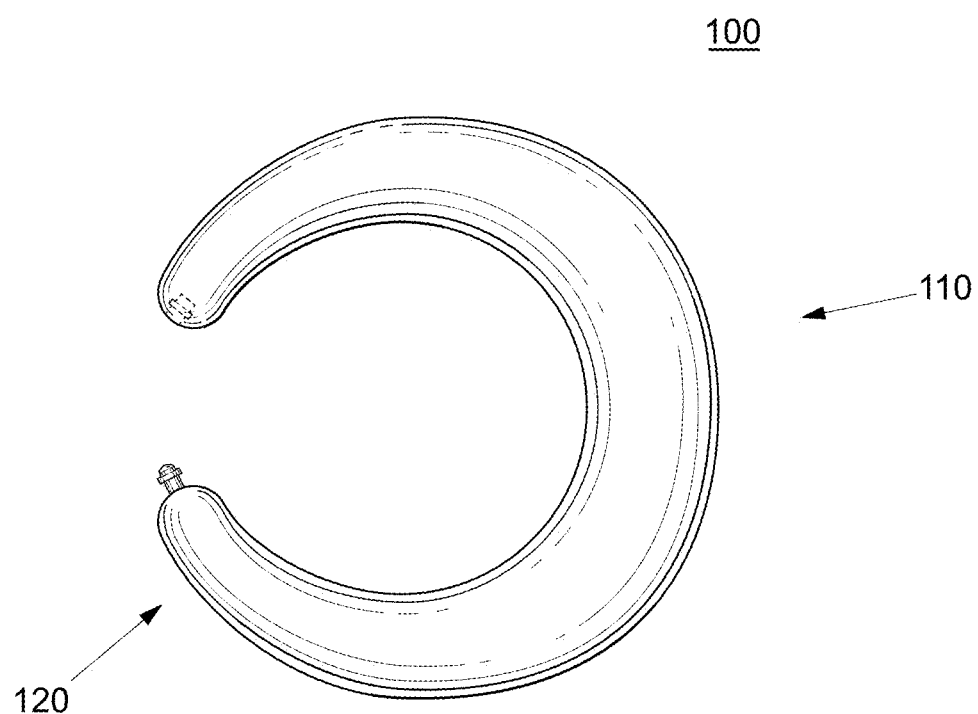

The ring-shaped body of the movement restriction device 110 may comprise an opening, or be possible to open, as indicated in FIG. 6 so as to allow the body to be arranged around the esophagus. After the movement restriction device 110 has been placed around the esophagus 20, the movement restriction device 110 may be affixed in a desired position, preferably at least partly above the cardia 22, by for example invaginating at least one of the first portion 110 and the second portion 120 by the outer wall of the stomach 10.

Figure 9:
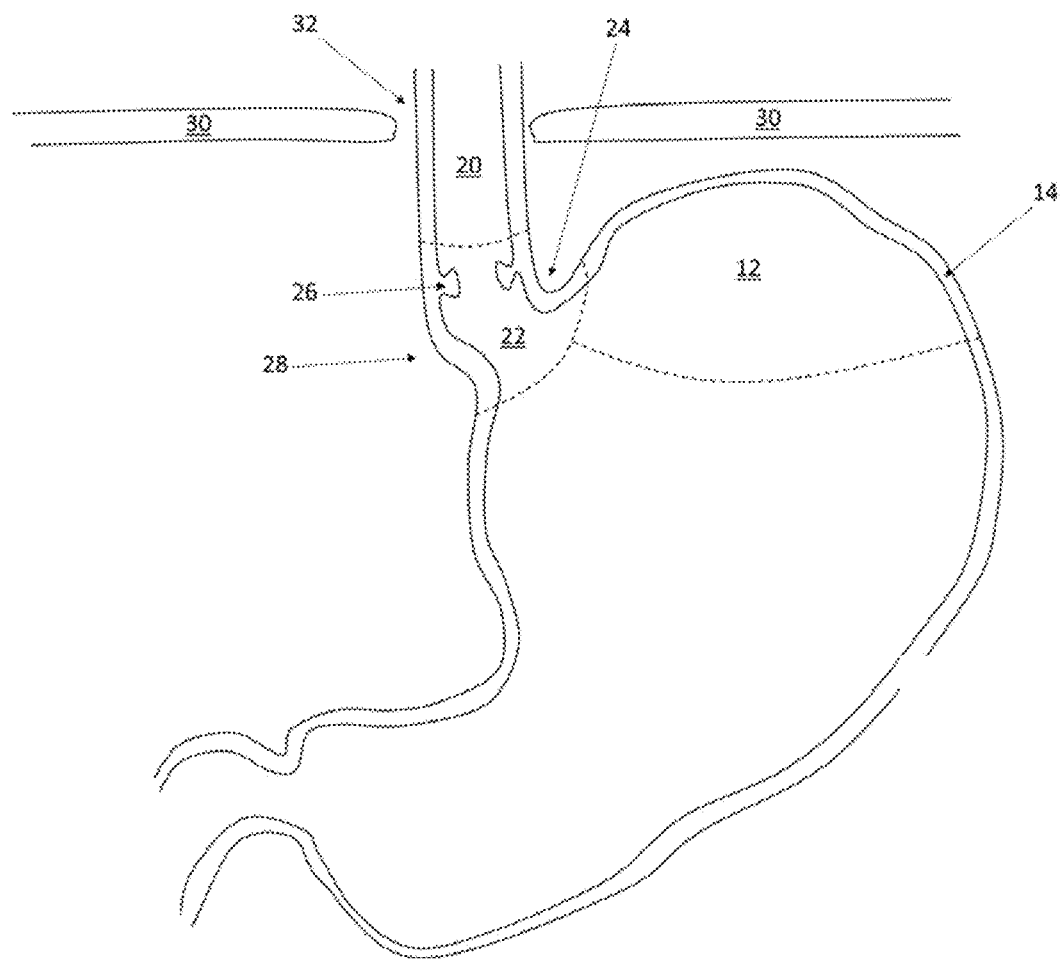
FIG. 9 is a schematic view of an exemplary stomach in which the apparatuses of FIGS. 1-6 may be implanted by means of the methods in FIGS. 7a-8b.

Further, the movement restriction device may be provided with a shape and size allowing for a gap to be defined and maintained between the second portion 120 and the side of the esophagus opposite to the fundus side, as illustrated in FIG. 9. Due to the affixation of the first portion 110 to the fundus 12, the separating gap between the second portion 120 and the tissue of the esophagus 20 may be maintained after implantation.

A method for implanting the apparatus 100 according in the body of a patient will now be discussed with reference to the examples illustrated in FIGS. 7a-c and 8a-b. The present method may be used for affixing an apparatus 100 in the desired position by invaginating or wrapping at least a part of the device in the fundus 12 of the stomach 10. Preferably, the following method may be used when implanting a movement restriction device for reinforcing the fundus 12 to interact with the diaphragm and hindering movement of the cardia 22 up into the thorax, as discussed with reference to the previous FIGS. 1-6. The method disclosed in connection with FIGS. 7a-c and 8a-b may thus be used for implanting a movement restriction device according to any of the previous embodiments.

Preferably, the apparatus 100 may be placed relatively high-up, above the upper edge of the lower esophageal sphincter (LES) so as to improve the effect on the reflux disease symptoms and allow the angle of His to assume its original, anatomically correct position and the LES to remain the abdomen. The present method can be divided into two separate parts: a first part in which a part of the stomach wall 14 is attached to the esophagus 20 so as to provide a "platform" positioning the apparatus 100 at the desired height, and a second part in which the apparatus 100 is placed in a pouch formed in the outside of the fundus, or wrapped in a portion of the fundus wall.

Figure 7A:
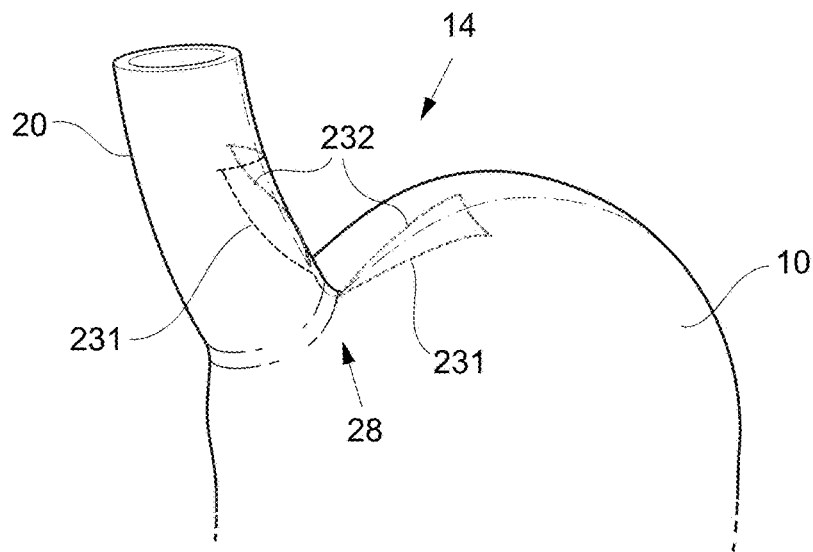
FIGS. 7a-8b are schematic views of various examples of methods for treating reflux disease and/or implanting an apparatus for treating reflux disease.
Figure 7B:
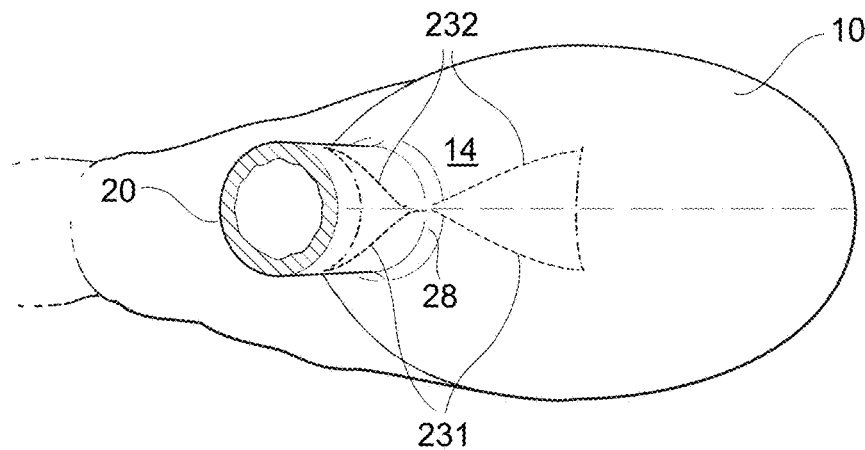
Figure 7C:
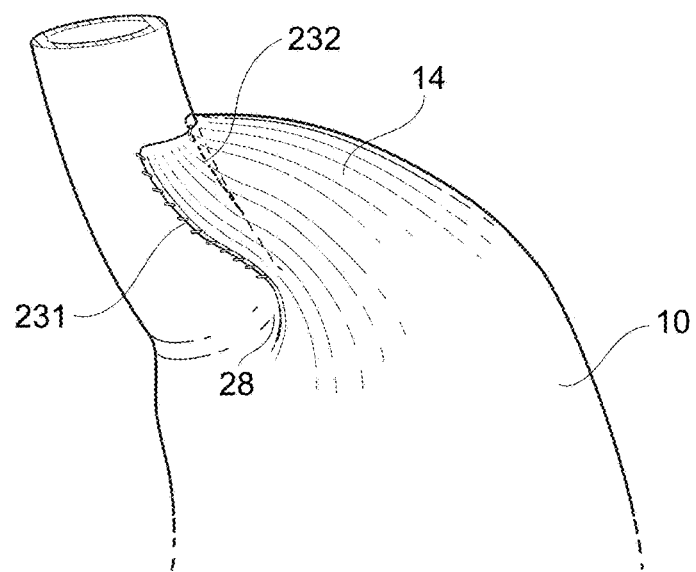

The first part of the method is illustrated in FIGS. 7a-c, wherein a fundus portion 14, extending from the angle of His 28 and in a direction away from the esophagus, is affixed to the esophagus 20 after the esophagus 20 has been dissected in mediastinum. According to the method, the fundus portion 14 may be folded towards the esophagus 20 such that the fundus portion 14 rests against the esophagus 20, from the angle of His 28 and upwards along the esophagus 20. The fundus portion 14 may then be affixed to the esophagus 20 by means of fasteners 230 arranged along a first line 231 and a second line 232. The first line 231 and the second line 232 may extend along the esophagus 20 and may be arranged such that a distance between the first line 231 and the second line 232 increases with an increasing distance from the angle of His 28. The positions of the first line 231 and the second line 232 are indicated by the dashed lines in FIGS. 22a and 22b, before the fundus portion 14 has been folded against and affixed to the esophagus 20. The fasteners 230 may for example comprise staples or sutures and may preferably be of a non-resorbable type). In case of the fasteners 230 comprise sutures, the first line 231 and the second line 232 may comprise a respective continuous suture.

The abdominal part of the esophagus 20 and the fundus 12 may be divided by a plane into a ventral and a dorsal side. In this case, the first line 231 may be considered to be arranged on the dorsal side of the plane, whereas the second line 232 may be arranged on the ventral side of the plane. The first line 231 and the second line 232 may in some example be placed at an angle of 45-75 degrees relative to the plane, such as for example 60 degrees. Put differently, a separating angle between the first line 231 and the second line 232 may be in the range of 90-150 degrees, such as for example 120 degrees. In some examples, the maximum separation between the two lines 231, 232, at the top of the lines 231, 232, may be about 2-3 cm, such as about 2.5 cm. The orientation of the lines of fasteners can be considered to describe a "V" or "Y", with the lines being separated at the top and gradually tapering towards each other towards the angle of His 28. Optionally, an additional fastener, such as a staple or suture, may be provided at the top of the "V" or "Y" shapes. Alternatively, a third line of sutures 233 may be provided between the first and second lines 231, 232.

In some examples, the method may comprise beginning the first line 231 less than 1 cm, such as about 0.5 cm, above the angle of His and beginning the second line 232 less than 3 cm, such as about 2 cm above the angle of His. Preferably, the second line 232 may be started less than 2 cm, such as about 1 cm, more ventral than the first line 231.

Figure 8A:
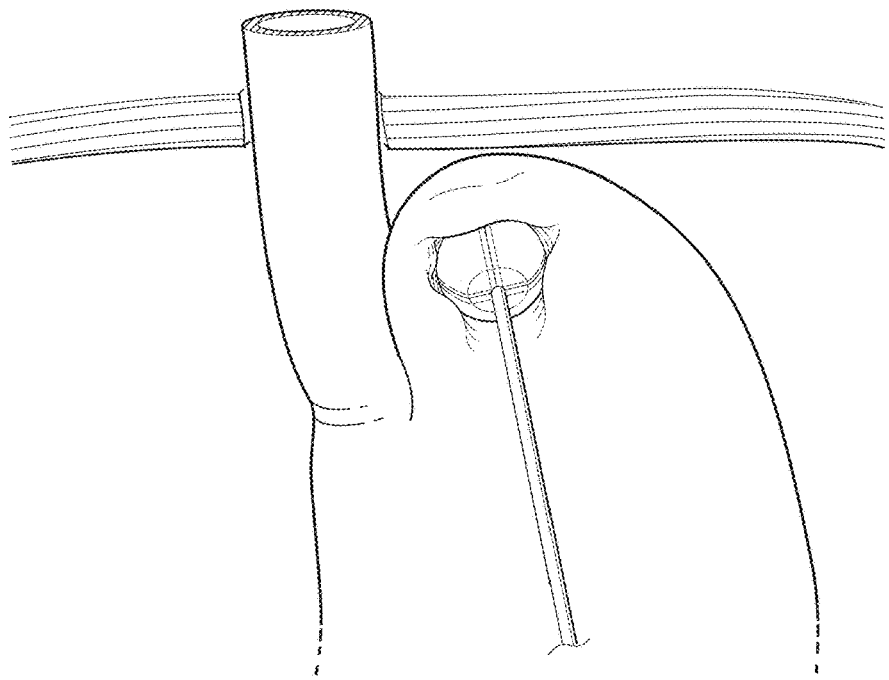
Figure 8B:
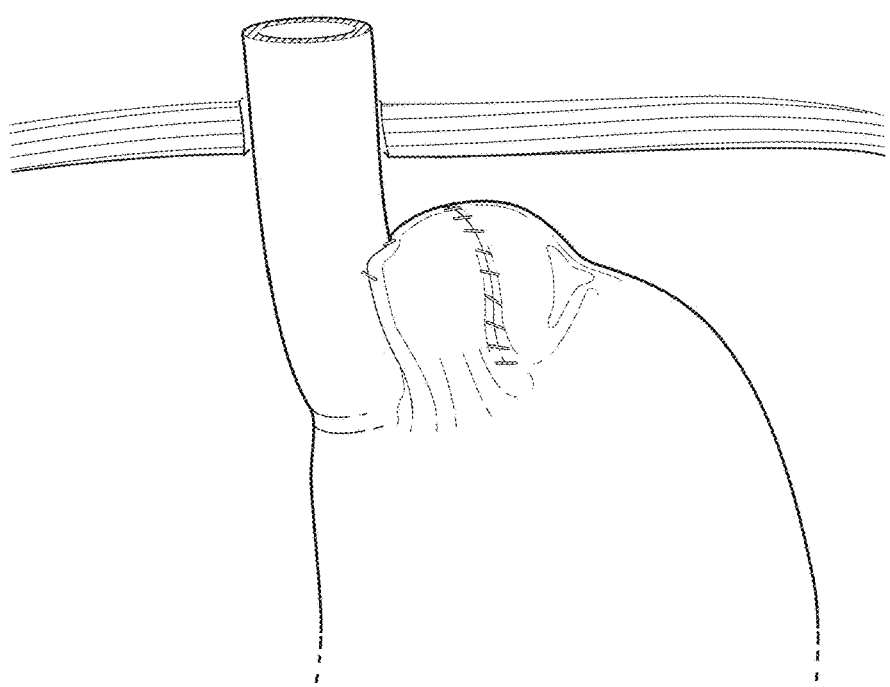

FIG. 8a shows the stomach 10 in FIGS. 7a-c after the fundus wall portion 14 has been affixed to the esophagus 20 according to the method outlined above. The method may now be followed by the implantation of the apparatus 100, such as for example the movement restriction device as shown in FIGS. 1-6. The apparatus 100 may be placed relatively high-up on the outside of the stomach fundus wall 12 and invaginated or covered by stomach tissue. This may be achieved by forming a pouch or recess 240 in the fundus 12, placing at least a part of the apparatus 100 in the pouch or recess 240, and at least partly closing the pouch or recess by fasteners 242 as illustrated in FIG. 8b. Preferably, the apparatus 100 is placed such that the top of the apparatus 100 is positioned at a distance from the LES that exceeds the total height of the apparatus 100 so as to reduce the risk of the LES sliding through the diaphragm opening 32. Alternatively, the top of the apparatus may be arranged further down, such at a distance from the LES exceeding half of the total height of the apparatus 100. Arranging the apparatus even further down may lead to an increased risk for the LES sliding into the thorax and thereby a malfunction of apparatus 100.

Preferably, the apparatus 100 is placed relatively close to the esophagus 20, such that the distance between the apparatus 100 and the esophagus 20 primarily is determined by the thickness of the doubled stomach wall 14 placed between the apparatus 100 and the esophagus 20. This distance may for example be less than 2 cm, such as less than 1.5 cm, depending on the thickness of the stomach wall 14.

As described above in connection with the embodiments illustrated in FIGS. 1-8, the apparatus may be implanted in the body so as to interact with different parts of the stomach and/or the esophagus. A first portion 110 of the apparatus may for example be affixed to the fundus 12 so as to function as a movement restriction device, and whereas a second portion 120 of the apparatus 100 may be arranged to at least partly encircle the esophagus 20.

FIG. 9 is a schematic cross section illustrating the general structure of a stomach of a healthy adult. The stomach is located in the patient's abdomen, below the diaphragm 30. Entering occurs through the esophagus 20, which may be an approximately 25 cm long fibromuscular tube passing from the thorax into the abdomen through an opening 32 in the diaphragm 30. The lower part of the esophagus 20 thus be referred to as the abdominal portion of the esophagus 20. The esophagus 20 may connect to the stomach via a shorter segment, typically less than 1 cm, called the cardia 22. The cardia 22 may hence be considered to form the junction or interface between the esophagus 20 and the stomach 10 and may be formed both of a portion of the esophagus 20 and a portion of the stomach. The cardia 22 may join the greater curvature of the stomach (to the right in the figure) in a cardiac notch 24, which creates an acute angle between the esophagus 20 and an upper stomach wall portion. The cardiac notch 24 may also be referred to as the angle of His. Typically, the angle may be around 75 degrees in a healthy adult. FIG. 39 further illustrates the cardiac sphincter 26, which may be located in the wall of the cardia 22. Functionally, the sphincter opens to allow food to pass into the stomach and then quickly closes to prevent stomach contents from flowing back into the esophagus 20. The fundus 12 is formed in the upper curved part of the stomach and may be located above the cardiac notch 24. It normally does not store food, but gas produced during digestion. The volume of an empty stomach of a healthy adult human may be around 50 ml, and the fundus 12 generally makes up a relatively small part of that volume. The outermost layer of the stomach wall is called serosa 14. The thickness off the serosa layer 14 may be around 1-2 mm, compared to the total stomach wall thicknesses which ranges from 3 to 4 mm. The serosa may extend also to the cardia 22 and may cover a lower portion of the esophagus 20. The serosa has been observed to cover the lower portion of the esophagus 20 extending to the cardiac sphincter 26, above which there may be no serosa layer on the outside of the esophagus.

The different aspects or any part of an aspect or different embodiments or any part of an embodiment may all be combined in any possible way. For example, all the embodiments relating to the apparatus or movement restriction device may be combined with the embodiments relating to the implantation methods. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way within the scope of the inventive concept, as defined by the appended claims. All examples herein should be seen as part of the general description and therefore possible to combine in any way in general terms.

The invention claimed is:

1. A method for treating gastroesophageal reflux disease by affixing a fundus portion of a fundus of a stomach of a human patient to an esophagus of the human patient, the method comprising:
   placing the fundus portion towards the esophagus,
   affixing the fundus portion to the esophagus by means of fasteners arranged along a first line of fasteners and a second line of fasteners,
   providing at least one additional fastener between the first line of fasteners and the second line of fasteners, at an upper portion of the affixed fundus portion,
   forming a pouch in the fundus,
   arranging a movement restriction device at least partly in the pouch, and
   invaginating at least a part of the movement restriction device by the fundus by at least partly closing the pouch with fasteners, wherein the movement restriction device is arranged at a position between a thoracic diaphragm of the human patient and a cardiac sphincter of the human patient to hinder the cardiac sphincter from sliding through an opening in the thoracic diaphragm into a thorax of the human patient.

2. The method according to claim 1, wherein a volume of the movement restriction device is non-adjustable after implantation.

3. The method according to claim 1, wherein the fasteners comprise sutures.

4. The method according to claim 1, wherein the movement restriction device is configured to change its shape to allow it to pass through a trocar during insertion into the body of the human patient.

5. The method according to claim 1, wherein the movement restriction device is formed of at least two distinct and separable pieces, and wherein the method further comprises assembling the pieces into the movement restriction device.

6. The method according to claim 1, wherein the movement restriction device is invaginated after affixing the fundus portion to the esophagus.

7. The method according to claim 1, wherein an abdominal part of the esophagus and the fundus are divided by a plane into a ventral and a dorsal side, and wherein the method comprises providing the first line of fasteners on the dorsal side of the plane and the second line of fasteners on the ventral side of the plane.

8. The method according to claim 1, wherein a maximum separation between the first line of fasteners and the second line of fasteners is in the range 2-3 cm.

9. The method according to claim 1, wherein the first line of fasteners starts less than 1 cm above the angle of His.

10. The method according to claim 1, further comprising dissecting the esophagus in mediastinum.

11. A method for treating gastroesophageal reflux disease by affixing a fundus portion of a fundus of a stomach of a human patient to an esophagus of the human patient, the method comprising:
    placing the fundus portion towards the esophagus,
    affixing the fundus portion to the esophagus by means of fasteners arranged along a first line of fasteners and a second line of fasteners, wherein the first line of fasteners starts less than 1 cm above the angle of His and the second line of fasteners starts less than 3 cm above the angle of His,
    forming a pouch in the fundus,
    arranging a movement restriction device at least partly in the pouch, and
    invaginating at least a part of the movement restriction device by the fundus by at least partly closing the pouch with fasteners, wherein the movement restriction device is arranged at a position between a thoracic diaphragm of the human patient and a cardiac sphincter of the human patient to hinder the cardiac sphincter from sliding through an opening in the thoracic diaphragm into a thorax of the human patient.

12. The method according to claim 11, wherein a volume of the movement restriction device is non-adjustable after implantation.

13. The method according to claim 11, wherein the fasteners comprise sutures.

14. The method according to claim 11, wherein the movement restriction device is configured to change its shape to allow it to pass through a trocar during insertion into the body of the human patient.

15. The method according to claim 11, wherein the movement restriction device is formed of at least two distinct and separable pieces, and wherein the method further comprises assembling the pieces into the movement restriction device.

16. The method according to claim 11, wherein the movement restriction device is invaginated after affixing the fundus portion to the esophagus.

17. The method according to claim 11, wherein an abdominal part of the esophagus and the fundus are divided by a plane into a ventral and a dorsal side, and wherein the method comprises providing the first line of fasteners on the dorsal side of the plane and the second line of fasteners on the ventral side of the plane.

18. The method according to claim 11, wherein a maximum separation between the first line of fasteners and the second line of fasteners is in the range 2-3 cm.

19. The method according to claim 11, wherein the second line of fasteners starts less than 2 cm more ventral than the first line of fasteners.

20. The method according to claim 11, further comprising dissecting the esophagus in mediastinum.

21. A method for treating gastroesophageal reflux disease by affixing a fundus portion of a fundus of a stomach of a human patient to an esophagus of the human patient, the method comprising:
    dissecting the esophagus in mediastinum,
    placing the fundus portion towards the esophagus,
    affixing the fundus portion to the esophagus by means of fasteners arranged along a first line of fasteners and a second line of fasteners,
    forming a pouch in the fundus,
    arranging a movement restriction device at least partly in the pouch, and
    invaginating at least a part of the movement restriction device by the fundus by at least partly closing the pouch with fasteners, wherein the movement restriction device is arranged at a position between a thoracic diaphragm of the human patient and a cardiac sphincter of the human patient to hinder the cardiac sphincter from sliding through an opening in the thoracic diaphragm into a thorax of the human patient.

22. The method according to claim 21, wherein a volume of the movement restriction device is non-adjustable after implantation.

23. The method according to claim 21, wherein the fasteners comprise sutures.

24. The method according to claim 21, wherein the movement restriction device is configured to change its shape to allow it to pass through a trocar during insertion into the body of the human patient.

25. The method according to claim 21, wherein the movement restriction device is formed of at least two distinct and separable pieces, and wherein the method further comprises assembling the pieces into the movement restriction device.

26. The method according to claim 21, wherein the movement restriction device is invaginated after affixing the fundus portion to the esophagus.

27. The method according to claim 21, wherein an abdominal part of the esophagus and the fundus are divided by a plane into a ventral and a dorsal side, and wherein the method comprises providing the first line of fasteners on the dorsal side of the plane and the second line of fasteners on the ventral side of the plane.

28. The method according to claim 21, wherein a maximum separation between the first line of fasteners and the second line of fasteners is in the range 2-3 cm.

29. The method according to claim 21, wherein the second line of fasteners starts less than 2 cm more ventral than the first line of fasteners.

30. The method according to claim 21, wherein the step of affixing the fundus portion to the esophagus is performed after the esophagus has been dissected in mediastinum.

\* \* \* \* \*